(12) United States Patent
Forster et al.

(10) Patent No.: US 11,771,461 B2
(45) Date of Patent: Oct. 3, 2023

(54) PASSIVE HOLDING DEVICE, MODULAR SURGICAL SYSTEM AND METHOD FOR MANIPULATING A TROCAR

(71) Applicant: KARL STORZ SE & Co. KG, Tuttlingen (DE)

(72) Inventors: Jonas Forster, Tuttlingen (DE); Chunman Fan, Tuttlingen (DE); Yaokun Zhang, Tuttlingen (DE)

(73) Assignee: KARL STORZ SE & CO. KG, Tuttlingen (DE)

( * ) Notice: Subject to any disclaimer, the term of this patent is extended or adjusted under 35 U.S.C. 154(b) by 525 days.

(21) Appl. No.: 17/065,989

(22) Filed: Oct. 8, 2020

(65) Prior Publication Data

US 2021/0113241 A1 Apr. 22, 2021

(30) Foreign Application Priority Data

Oct. 21, 2019 (DE) ............... 10 2019 128 277.2

(51) Int. Cl.
| | |
|---|---|
| *A61B 17/34* | (2006.01) |
| *A61B 90/50* | (2016.01) |
| *A61B 1/00* | (2006.01) |
| *A61B 17/00* | (2006.01) |

(52) U.S. Cl.
CPC .......... *A61B 17/3468* (2013.01); *A61B 90/50* (2016.02); *A61B 1/00149* (2013.01); *A61B 2017/00039* (2013.01); *A61B 2017/00075* (2013.01); *A61B 2017/00477* (2013.01); *A61B 2017/3492* (2013.01); *A61B 2090/508* (2016.02)

(58) Field of Classification Search
CPC . A61B 17/3468; A61B 90/50; A61B 1/00149; A61B 2017/00039; A61B 2017/00075; A61B 2017/00477; A61B 2017/3492; A61B 2090/508; A61B 34/20; A61B 2017/347; A61B 2090/506
See application file for complete search history.

(56) References Cited

U.S. PATENT DOCUMENTS

| | | | |
|---|---|---|---|
| 5,824,007 A | 10/1998 | Faraz et al. | |
| 6,406,472 B1 * | 6/2002 | Jensen | ................... B25J 9/1065 606/1 |
| 2021/0282889 A1 * | 9/2021 | Sasai | ...................... F16M 13/02 |

* cited by examiner

*Primary Examiner* — Diane D Yabut
*Assistant Examiner* — Rachel S Highland
(74) *Attorney, Agent, or Firm* — Eversheds Sutherland (US) LLP (57) ABSTRACT

The present application provides a passive holding device for handling a trocar and a modular surgical system. The passive holding device has a fastening device with a coupling portion. A pivoting mechanism is connected to the coupling portion via a rotary joint. The pivoting mechanism has two L-shaped branches arranged parallel to one another, each having a short leg that is connected to a long leg via a pivot joint. The short leg of the first branch is longer than the short leg of the second branch and is connected to the long leg via a rotary shaft. The trocar holder has a gripping device and has an instrument brake. A tilting brake is arranged at the coupling portion, operatively connected to the rotary joint, and a pivoting brake is arranged at the coupling portion operatively connected to at least one of the terminal pivot joints.

10 Claims, 5 Drawing Sheets

PASSIVE HOLDING DEVICE, MODULAR SURGICAL SYSTEM AND METHOD FOR MANIPULATING A TROCAR

TECHNICAL FIELD

The invention relates to a passive holding device for handling a trocar, a modular surgical system having such a holding device, and a method for handling a trocar using the passive holding device.

BACKGROUND OF THE INVENTION

It is known from the prior art that the handling of surgical instruments during a microsurgical operation can be simplified in order to relieve the surgeon and the surgical team. On the one hand, surgical robots are known that take on specific tasks automatically. On the other hand, electronically controllable instruments can be used that can be remotely controlled. However, such devices are complex and space-filling and lead to a greater spatial distance between surgeon and patient, which is not desired for many applications.

Passive holding devices for surgical instruments have therefore also been developed with which the instrument can be clamped, wherein all degrees of freedom of movement about the trocar point are prevented at the same time and wherein the fixation must be released again to change the position. Both clamping and releasing are usually done manually. There are also holding devices that can be applied to a trocar specially adapted for this purpose, so that the possibilities for using various instruments are limited.

US 2012/0296281 A1 describes a holding device for microsurgical instruments, wherein a rotary point at which there are degrees of freedom for movement of the instrument is provided via a ball, which is a specially shaped part of the trocar, which is clamped in a half-shell or a ring and can be moved when releasing the clamping. The rotary point is therefore outside the patient's body in the surgical application.

SUMMARY OF THE INVENTION

Based on this prior art, the object of the present invention is to provide an improved holding device for handling any trocar, with which a surgical operation can be carried out more gently. This object is achieved by a passive holding device with the features in accordance with claim 1.

The further object of providing an expandable system with which a plurality of surgical instruments can also be easily handled is achieved by a modular surgical system with the features in accordance with the independent claim 7.

Furthermore, the object of being able to change the position of a trocar gently is achieved by the method for handling a trocar with the features of independent claim 10.

Preferred embodiments of the passive holding device, the modular surgical system, and the method are set out in the dependent claims.

According to a first embodiment, a passive holding device according to the invention has a fastening device having a coupling portion for handling a trocar with which a surgical instrument is held or guided during a surgical operation. The trocar can be fastened to a connecting device via a trocar holder and can be fastened to the fastening device via this connecting device. According to the invention, a pivoting mechanism is connected to the coupling portion via a rotary joint located in the coupling portion so as to be rotatable about a horizontal axis of the coupling portion and thus forms the connecting device. The pivoting mechanism has two L-shaped branches arranged parallel to one another, each of which has a short leg which is connected to a long leg via a pivot joint. On the side facing the coupling portion, the short legs of each branch lying next to one another with an elongated holding portion of the fastening device are each connected via a terminal pivot joint. Furthermore, the short leg of the first branch is longer than the short leg of the second branch. It is arranged at a distal end of the elongated holding portion and is connected to the long leg of the second branch over a rotary shaft. The trocar holder, which has a gripping device which can be brought into engagement with the trocar, and which has an instrument brake for the operative coupling with the surgical instrument, is pivotably attached to a distal end of the pivoting mechanism. Furthermore, a tilting brake is arranged at a proximal end of the coupling portion and is operatively connected to the rotary joint located in the coupling portion, and a pivoting brake is arranged on the coupling portion, which is operatively connected to at least one of the terminal pivot joints of the pivoting mechanism.

The passive holding device provides four degrees of freedom for the movement of the surgical instrument at a stationary rotary point on the trocar: "Pivoting" or pivoting movement is referred to herein as a movement by the pivoting mechanism that takes place within an imaginary plane (pivoting plane) defined by the pivoting mechanism and parallel to it; the pivot axis of the trocar runs through the rotary point. Viewed from the proximal end of the passive holding device, this corresponds to a back and forth movement of the instrument tip, i.e., the distal end of the surgical instrument. By contrast, "tilting" or tilting movement is understood to mean the movement (rotation) around the horizontal axis of the elongated holding portion as a tilting axis that takes place using the rotary joint in an imaginary plane (tilting plane) that is orthogonal to the pivoting plane. Viewed from the proximal end of the passive holding device, this corresponds to a movement of the instrument tip to the right or left. Tilting also tilts the pivoting plane, pivoting also pivots the tilting plane; the rotary point is always in both planes. While these two degrees of freedom are provided by the connecting device and the fastening device by changing the holding position of the trocar, the other two degrees of freedom are present on the instrument within the trocar. This involves rotation, i.e., a rotation of the surgical instrument around its own axis, and translation, i.e., a displacement along the instrument axis, whereby the penetration depth is set.

Thanks to the brakes, these degrees of freedom of movement can be slowed down or prevented, so that the position of the instrument, i.e., both the location in particular of the instrument tip and the alignment of the instrument, is fixed and both the surgeon and assistant doctor, etc. have their hands free again. Translation and rotation are allowed or prevented by activating and deactivating the instrument brake. Independently of this and independently of each other, the tilting brake can be used to prevent tilting and the pivoting brake can be used to prevent pivoting.

Nevertheless, the surgical instrument can be operated manually as required and the haptic feedback, which is missing with remote-controlled instruments or has to be simulated in a complex manner, is retained.

The terms "active" and "passive" in relation to the holding device are based on whether or not motorized electronic control or operability for the surgical instrument is provided by the holding device. With the passive holding device, no actions are carried out on the patient, since the surgical instrument that is held or guided by the trocar held therewith is not operated by the holding device, but is merely positioned and held indirectly. Independently of this, the actuation of the holding device itself can take place both manually and in a motorized manner, i.e., adjusting a position of the holding device can, for example, also be done electronically. As a surgical instrument, by which a microsurgical instrument is meant herein, both instruments for manipulation such as scalpels, grippers, or electrosurgical instruments as well as instruments for measuring and detecting, for example endoscopes, are included that are guided through a trocar or held in it.

The terms "distal" and "proximal" used herein to describe position information on the holding device and on its parts, as well as in relation to the surgical instrument that can be indirectly guided with it, are to be understood in relation to the user, e.g., a surgeon, i.e., "distal" is a part that is further away from the user in normal use, whereas "proximal" means a part that comes closer to the user.

A fixed, stationary rotary point, or trocar point, which is common to the pivoting and tilting, is advantageously determined by the passive holding device. When used in surgery, this rotary point is at the point of entry into the tissue, e.g., in the abdominal wall during a laparoscopic surgical operation. Since the movement around the rotary point is brought about from a remote location, the rotary point can be placed directly in the point of entry. This advantageously avoids stress and trauma to the tissue around the point of entry and the operation can be carried out more gently. At the same time, moving the trocar around the rotary point requires less effort on the part of the surgeon.

In addition, this position of the rotary point makes it possible to use the full range of movement that is necessary for changes in position of the trocar placed in the point of entry without repositioning the passive holding device as a whole. Such repositioning during an operation is tedious and lengthy and can also lead to additional stress for the patient.

The fact that the trocar or the surgical instrument can be fixed in any position and orientation and does not have to be held by personnel is also advantageous for a surgeon in the sense of solo surgery if a plurality of holding devices are used for the usage of a plurality of or different instruments. Subsequently, after an instrument has been placed, it can be fixed in place and changed to operate another instrument in a simple manner. Thereby, less personnel is required and costs are avoided.

According to a further embodiment, the trocar holder is coupled to the long legs of the branches of the pivoting mechanism via a respective connecting shaft. In this way, the pivotable attachment of the trocar holder to the pivoting mechanism is provided via the connecting shafts without great structural effort. A movement triggered at a joint of the pivoting mechanism can thus be transferred to the trocar holder and into a pivoting movement.

Embodiments of the passive holding device are conceivable that are completely manually adjustable, but they are preferably designed as those that can be mechanically operated, e.g., are operated by an electric motor, or that combine the two.

In a further embodiment of the passive holding device according to the invention, the pivoting mechanism is designed to be retracted. Starting from a center position within the pivoting plane, the holding device can be pivoted in two directions (forwards and backwards) and within the tilting plane in two directions (to the right and left), between which it is possible to switch as desired. The ability to retract is essential for the manageability for the surgeon, since he is not limited to a holding position that has been set once and can change the holding position with simple movements, which is not a problem thanks to the fixed rotary point. In addition, the ability of the joints to be retracted is a safety feature for mechanically adjusted holding devices in the event of a malfunction or an emergency shutdown.

The group of brakes of the passive holding device includes the instrument brake, the tilting brake, and the pivoting brake. According to yet another embodiment, at least one of these brakes, but preferably each of these brakes, is designed as a passive brake. In this case, "passive brake" is understood to mean that the brake is de-energized, i.e., the braking effect is maintained even when de-energized. In other words, the braked state is set without any intervention, so that the current position is always held and fixed. On the other hand, the respective brake must be released briefly in order to be able to bring about a change in position. For this purpose, the tilting brake and pivoting brake for control are preferably coupled with the actuation of the pivoting mechanism, so that the release of the respective brake is triggered immediately when one of the terminal pivot joints or the rotary joint is deflected.

Another embodiment of the passive holding device provides a sensory measuring unit which is designed to determine a change in position or orientation of the surgical instrument. For this purpose, a sensory measuring unit can be present on the pivot joint, which is designed to detect a tilting movement of the holding device. Alternatively or additionally, a sensory measuring unit can be present on one or more of the terminal pivot joints, which is designed to detect a pivoting movement of the holding device. Sensors of the sensory measuring unit are preferably located on the braked joints, in particular on the tilting brake and/or on the pivoting brake, and can more preferably be fed by the same energy supply. A sensory measuring unit can also be present on the trocar holder, which is designed to detect a translational and/or rotational movement of the surgical instrument. In each case, the sensory measuring unit has at least one sensor, which is preferably an inertial sensor, in particular a position, acceleration, or rotation rate sensor. A sensory measuring unit can also have a plurality of sensors, for example an inertial measuring unit, the detected values of which are combined for evaluation in order to determine the position information.

Depending on where they are arranged, the sensory measuring units can detect the movement triggered there and send the measured values to an evaluation unit. For this purpose, a common evaluation unit can be sufficient for all collected measurement data, but they can also be evaluated separately in advance, i.e., for each measuring unit, and only then combined. In a suitable manner, such an evaluation unit should not be present directly on the holding device as part of the sensory measuring unit, since the holding device must be treated for reasons of hygiene, for example by autoclaving. In principle, the raw data collected by the sensors can be tapped and evaluated separately.

Furthermore, an output unit can be provided which is preferably arranged externally to the holding device, which output unit passes on the detected value, which corresponds to a change in position (through translation) or change in position (through pivoting, tilting, or rotation) or, in the case of a combination of three measuring units, their superposition, for further use, and, for example, visualizes it on a screen display, saves it for subsequent evaluation and analysis, or branches it off as input for further processes.

In an embodiment in which both one of the terminal pivot joints and the rotary joint and the trocar holder are equipped with sensors, complete instrument tracking is possible, i.e., the exact position of the instrument tip, which is located in the patient's body during an operation, and the alignment of the surgical instrument can be determined at any time. This makes it possible to feed the evaluated data into a control unit, for example an endoscope, so that it can be controlled and possibly moved as a function of the movement of the instrument.

Another embodiment provides that the sensor of the sensory measuring unit, which is present on the trocar holder, is a roller wheel. This lies against the surgical instrument guided in the clamped trocar and is rolled when the instrument moves in a translatory manner. The penetration depth of the instrument can be deduced from the rolled distance of the roller wheel or the number of (proportional) revolutions. If necessary, an additional sensor, possibly also a further roller wheel, can be present in order to detect the rotation of the surgical instrument.

Alternatively, the sensor of the sensory measuring unit on the trocar holder can also be a magnetic sensor or a capacitive sensor which is designed to interact with a magnetic measuring tape or capacitive measuring tape present on the surgical instrument that is attached to the trocar for signal transmission. From the relative change in position detected in the sensory measuring unit between the magnetic sensor and the magnetic measuring tape or between the capacitive sensor and the capacitive measuring tape when the surgical instrument is moved, conclusions are drawn as to its translation and rotation.

The invention also relates to a modular surgical system. The modular surgical system comprises at least one passive holding device according to the invention, as stated above, and a trocar held by it, as well as a surgical instrument which is held or guided by the trocar. In this case, "modular" means that the system can be expanded to include holding devices, each with a trocar and surgical instrument, and also with modules for position determination and control, with which the system can be partially automated.

In a simple form, the modular surgical system thus has only one holding device with trocar and surgical instrument, which can be sufficient for simple operative operations or as an extension of an already existing system. If the surgical instrument is an endoscope, an endoscopic examination can easily be carried out.

In order to provide a comprehensive surgical system, however, the system can have a plurality of holding devices, which can be both active and passive holding devices, in which, depending on the application, different trocars, but in particular different surgical instruments, can be held and operated. For example, a solo surgery station can be set up that only has passive holding devices, one holding device being used to hold an endoscope and further holding devices being used to hold an additional surgical instrument. The surgeon can do without an assistant and switch between different instruments, which he operates manually, while the other instruments are fixed.

In a further embodiment, the modular surgical system has a position determination system with an output unit and at least two holding devices. At least one of the holding devices is an active holding device which has a control unit operatively coupled to the output unit and is designed to automatically move a further surgical instrument received in the active holding device. An active holding device is understood in this case to be a holding device in which the actuation of the surgical instrument takes place in a motorized manner via the holding device. The remaining holding devices can be passive; any extensions with passive and active holding devices are possible. The position determination system is used to determine the position of the surgical instrument held and guided in the passive holding device via the trocar, including the position, location, and alignment of the instrument tip. Depending on this detected position or movement as a change in position or orientation, the further surgical instrument is controlled via the control unit to which the current position information is transmitted from the output unit. The further surgical instrument is preferably an endoscope which, coupled to the change in position and orientation of the surgical instrument, is automatically moved along in the passive holding device in order to image the respective region of interest around the instrument tip.

With a plurality of passive holding devices, the position determination can be limited to one of the surgical instruments held therein or refer to a plurality of instruments, wherein preferably a switching operation between the surgical instruments is possible in order to couple the control unit for the further surgical instrument, in particular for an endoscope. Alternatively, an evaluation algorithm that includes a plurality of instrument positions can be used to determine a meaningful position for the endoscope, and the endoscope can be positioned and aligned there using the control unit.

One embodiment of the modular surgical system provides that the position determination system is provided via sensory measuring units present on the passive holding devices and an associated evaluation unit, as described above for the passive holding device, wherein the evaluation unit preferably is separate and not interfering with hygiene treatments of the holding device. This type of position determination, in which the movement that is transmitted to the surgical instrument is detected directly via sensors arranged on the joints or brakes, and thus the current position of the surgical instrument is calculated, allows the position to be precisely detected with little calculatory effort.

In a further embodiment, an optical and/or electromagnetic position determination system can be provided. Such position determination systems are known from the prior art, for example, the instrument movement is recorded and analyzed via a camera or a camera system or via electromagnetic measurement fields that can also penetrate bodies, the surgical instrument being equipped with light-emitting or reflecting reference bodies or magnetic reference bodies.

Furthermore, it is conceivable that not only an endoscope but also another surgical instrument is controlled as a function of the detected movement of another instrument. In principle, however, the surgeon can still handle it. In contrast to the use of an alternatively usable surgical robot, the surgeon always receives haptic feedback of his actions on the patient and contact with the patient is maintained thanks to the compact, space-saving construction of the modular surgical system.

In addition, the modular surgical system can also be designed for control via a screen on which the image information or data from the position determination system collected by means of the endoscope are reproduced. Input commands can be entered, converted, and used to control the modular surgical system, or more precisely its active components, both via a computer mouse and via control buttons or foot switches.

The method according to the invention for operating a passive holding device according to the invention is used for handling a trocar with which a surgical instrument can be held or guided during a surgical operation and which is fastened to the passive holding device via the trocar holder.

The method comprises the step that, when a stationary rotary point is held, a change in position of the trocar is effected by actuating the pivoting mechanism. Any transfer of the trocar from a starting position to a position that has changed compared to this starting position is considered a change in position. Any position that the trocar can assume within the holding device can serve as a starting position for a (further) change in position.

Actuating the pivoting mechanism is in particular the deflection of one of the pivot joints of the pivoting mechanism, preferably one of the terminal pivot joints, by a predetermined pivot angle in a predetermined direction. In addition, the pivoting mechanism can also be actuated by deflecting the rotary joint present in the coupling portion by a predetermined tilt angle in a predetermined direction. The change in position of the trocar is brought about by a change in position of the trocar holder, which is set by one of these forms of actuation alone or by executing them sequentially or in parallel.

The method according to the invention protects the point of entry into the patient when the trocar, in order to provide access for a surgical instrument, has been placed there and is held in the trocar holder of the passive holding device. Since the stationary rotary point is then set so that it lies in the point of entry, it is not widened or is widened only to a minimal extent when the position of the trocar changes. The point of entry is thus less irritated than is the case with a manual grip on the trocar or when positioning with a device whose rotary point, due to the design, can be arranged outside the body and therefore not in the point of entry.

A further embodiment of the method provides that the actuation of the pivoting mechanism comprises releasing the pivoting brake before one of the terminal pivot joints is deflected and/or releasing the tilting brake before the rotary joint located in the coupling portion is deflected. Furthermore, the respective brakes can be locked after the change in position of the trocar. As a result, the device and thus the position of the trocar is fixed and a change in position can only take place by consciously controlling the respective braked joints. Inadvertent adjustment is practically impossible.

The method can be carried out both manually and electronically supported and also operated completely electronically, the passive holding device in each case having the necessary operating elements such as levers or switches, which are known to the person skilled in the art.

BRIEF DESCRIPTION OF THE DRAWING

Further embodiments as well as some of the advantages associated with these and further embodiments will be made clearer and better understood from the following detailed description with reference to the accompanying drawings. Objects or parts thereof that are substantially the same or similar can be provided with the same reference signs. The drawings are only a schematic representation of an embodiment of the invention.

In the drawings.

DETAILED DESCRIPTION

Figure 1:
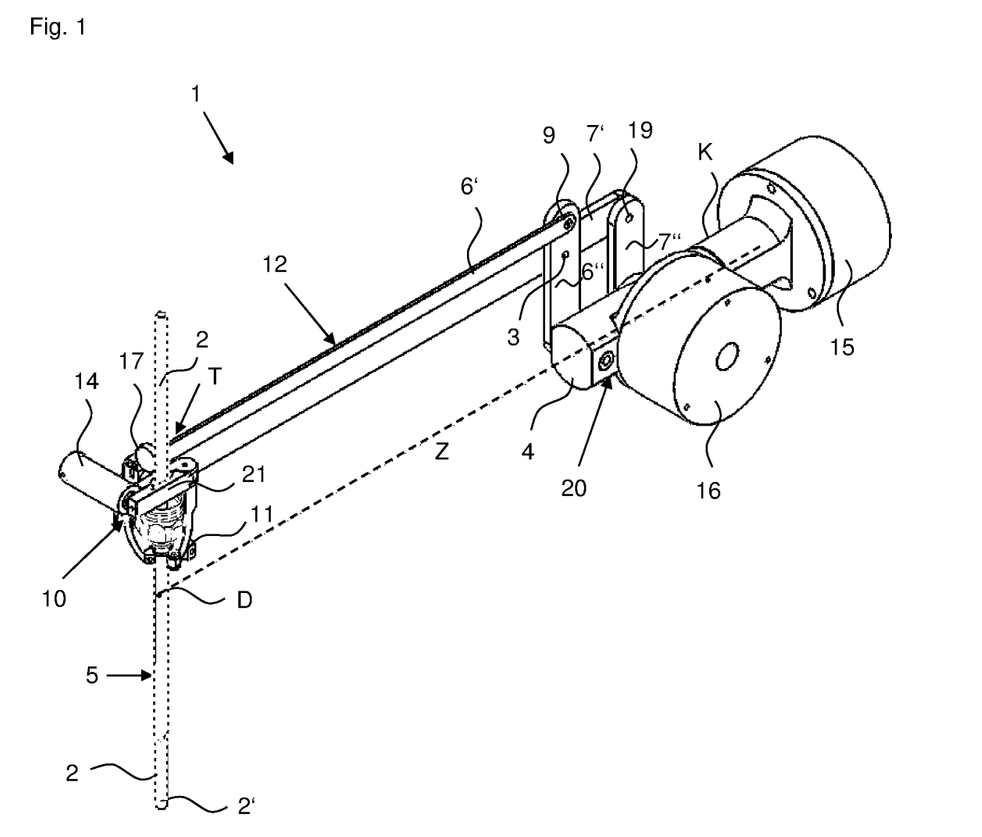
FIG. 1 is a perspective view of the passive holding device with a fastened trocar.
Figure 2:
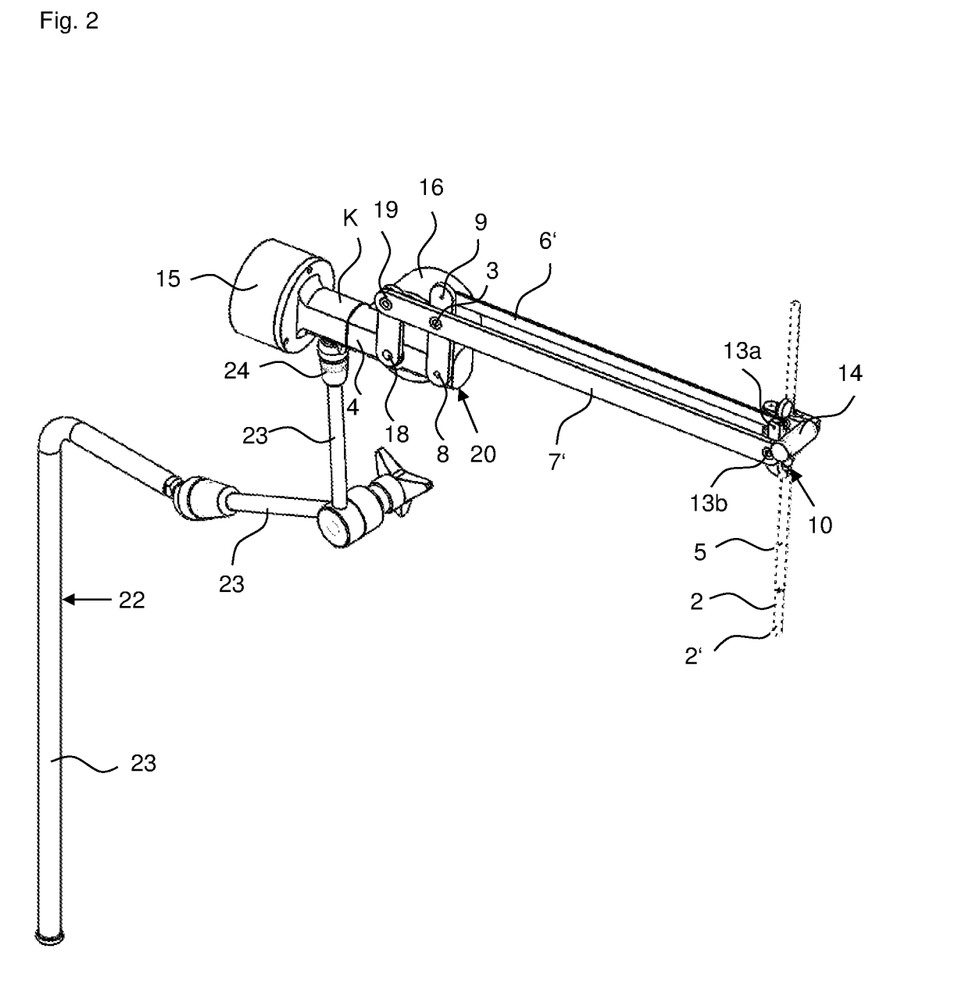
FIG. 2 is a perspective view of the passive holding device with fastened trocar, coupled to a tripod.

The passive holding device 1 according to the invention is shown in various positions in FIGS. 1 to 7, a trocar 5 and a surgical instrument 2 each being received in the passive holding device 1, which are not part of the device 1 as such and are therefore drawn with dashed lines in FIGS. 1 and 2, and assume different positions depending on the orientation of the holding device 1.

In FIG. 2, the passive holding device 1 is set up by a tripod 22 or a stand device 22 and positioned in the room. This can also be the tripod 22 of a robot arm. The height and the distance to the operating table or patient can be adjusted via a plurality of articulated tripod arms 23. The passive holding device 1 is detachably connected to the stand 22 via the connector 24 and can be removed again if necessary.

The holding device 1 has a fastening device 20 which is formed partly by a coupling portion K and another part by the elongated holding portion 4. In addition to the pivoting mechanism 12, the entire holding device 1 can also be coupled to a stand 22 via the coupling portion K.

The pivoting mechanism 12 forms the connecting device from the fastening device 20 to the trocar holder 10, which is arranged at the distal end T of the pivoting mechanism.

The pivoting mechanism 12 has two branches 6, 7, each with a short leg 6", 7" and a long leg 6', 7'. The short leg 6", 7" is connected to the long leg 6', 7' via a pivot joint 9, 19. The two branches 6, 7 are connected to one another in that the short leg 6" of the first branch is connected to the long leg 7' of the second branch via the rotary shaft 3. The rotary shaft 3 represents a connecting shaft that is not spatially fixed, about which the two legs 6", 7' connected to one another can be rotated relative to one another. The branches 6, 7 are connected to the elongated holding portion 4 of the fastening device 20 at the first ends of their short legs 6", 7" via two terminal pivot joints 8, 18 (cf. FIG. 2 and FIGS. 5 to 7). The two terminal pivot joints lie on a common axis that is parallel to the horizontal axis Z of the elongated holding portion 4. At which point on the lateral surface of the elongated holding portion 4 the terminal pivot joints 8, 18 are arranged can vary in other embodiments; it is crucial that a connecting line passes through the two terminal pivot joints 8, 18, parallel to the horizontal axis Z, which is also the rotary shaft of a pivot joint lying in the coupling portion K, so that a common rotary point D is present. The short leg 6" of the first branch 6 is longer than the short leg 7" of the second branch 7; at the same time the long leg 6' of the first branch 6 is shorter than the long leg 7' of the second branch 7. As a result, in the position shown in FIG. 1 and FIG. 2, the long leg 6' of the first branch 6 lies above the long leg 7' of the second branch. The long legs 6', 7' of the branches 6, 7 are connected to the trocar holder 10 via connecting axes 13a, 13b, which, like the rotary shaft 3, allows relative rotation between the trocar holder 10 and the respective long legs 6', 7'.

Figure 3:
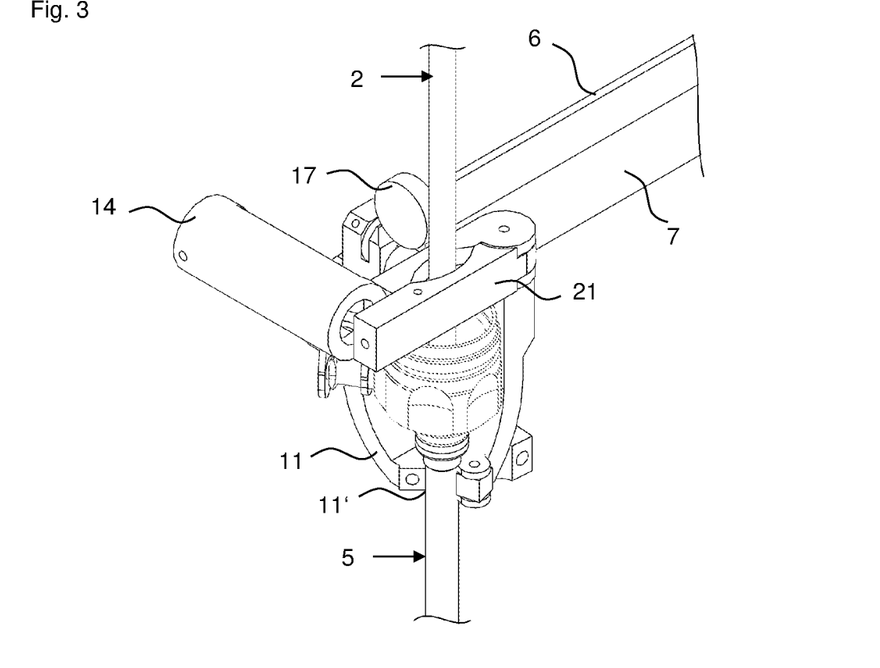
FIG. 3 is a detailed view of the trocar holder of the passive holding device with the trocar fastened thereto.

The trocar holder 10 is shown in more detail in FIG. 3 in a detailed view. It has a gripping device 11 which partially engages around the side of the trocar 5 and holds it in that a tubular part of the trocar 5 is guided through a receptacle 11' of the gripping device 11. The gripping device 11 can be designed to be flexible or movable in such a way that the size of the receptacle 11' can be adapted for trocars 5 which have different sizes and differ in particular in diameter, but also in other forms. In other words, the receptacle 11' is expanded or narrowed when the gripping device 11 is opened or closed.

It goes without saying that the trocar holder can also be constructed differently in order to be able to hold a trocar. It is crucial that the trocar can also be received in the trocar holder after it has been set, i.e., after it has pierced a barrier (skin, tissue, etc.) in order to provide access to a space inside the body. For this purpose, the trocar holder can also be constructed in two or more parts, the individual parts being brought into engagement with the trocar from different sides and/or from above/outside, i.e., from the proximal side.

Since the trocar holder is not fixed to a specific trocar or a determined trocar shape, the trocar to be clamped can consequently also differ from the representations shown in this case, in particular in terms of length, diameter, shape of the proximal end, and shape of the distal end.

On the trocar holder 10, there is also an instrument brake 14 which cooperates with a clamp 21 which encompasses the surgical instrument 2 above the trocar 5 and, when the instrument brake 14 is active, prevents the surgical instrument 2 from a movement relative to the trocar 5, of the trocar holder 10 and thus the passive holding device 1, in that it is firmly enclosed. If the instrument brake 14 and thus the clamp 21 is released, the surgical instrument 2 can both be rotated about its own axis and also be displaced translationally along this axis.

Figure 5:
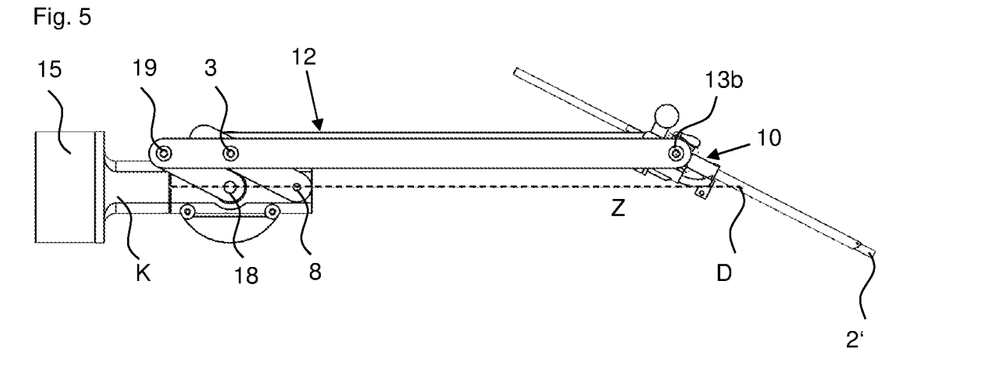
FIG. 5 is a side view of the passive holding device in a pivoted position.
Figure 7:
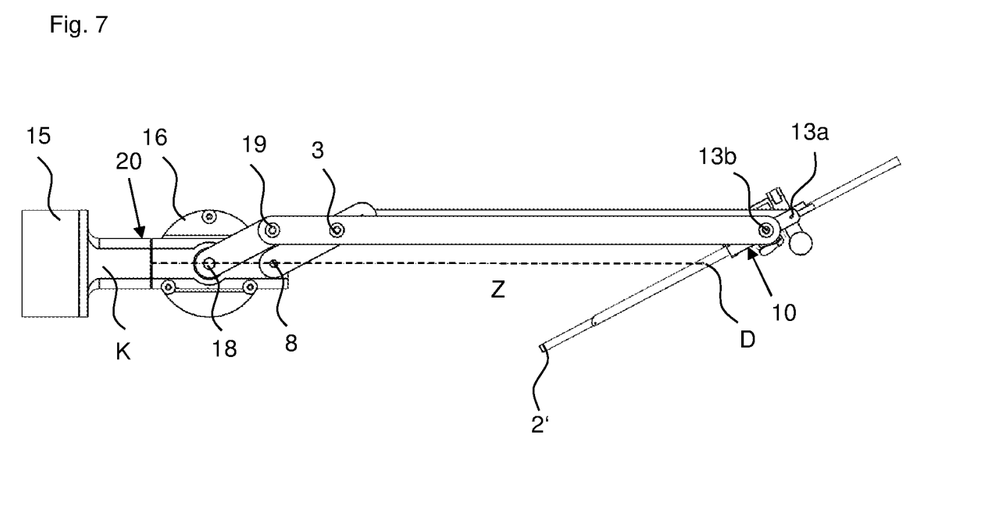
FIG. 7 is a side view of the passive holding device in a further pivoted position.

In the comparison of FIG. 5 to FIG. 7, a degree of freedom of movement of the surgical instrument 2 is illustrated, namely the translation along the axis of the instrument 2, which is at the same time the axis of the trocar 5. The instrument tip 2' protrudes further out of the trocar 5 in FIG. 7 than in FIG. 5. This movement is allowed in that the instrument brake 14 is released and the clamp 21 no longer holds the surgical instrument 2. In this way, a rotation of the surgical instrument 2 about its axis can also be brought about (not shown in drawings). Tilting and/or pivoting movements of the surgical instrument, however, are only possible by moving specific parts of the passive holding device 1.

Figure 6:
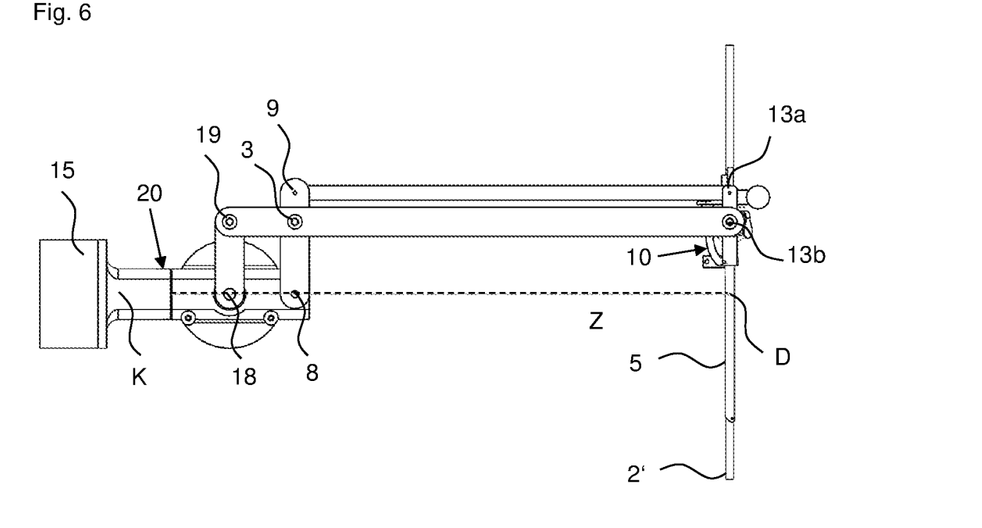
FIG. 6 is a side view of the passive holding device in the center position.

FIGS. 5 to 7 illustrate the functionality of the pivoting mechanism 12. Since the branches 6, 7 are connected via the rotary shaft 3, a change in the angle of a terminal pivot joint 8, 18 always causes changes in the position of the other parts of the pivoting mechanism 12, which relate to the trocar holder 10 and thus indirectly also to a clamped trocar 5 and a surgical instrument 2 that can be transferred therein. At least one of the terminal pivot joints 8, 18 is actuated by being deflected by a predetermined pivot angle which, starting from the center position shown in FIG. 6, can lie in a range of 80° in both directions, i.e., from +80° bis −80°. As a result, the short legs 6", 7" of the branches are pivoted about the respective terminal pivot joint 8, 18. In the view shown, starting from the starting position in FIG. 5, for example one of the short legs 6", 7" is rotated clockwise; the other short leg 6", 7" follows the movement, i.e., it is erected in FIG. 5 to FIG. 6. At the same time, the long legs 6', 7' which are and remain always aligned parallel to the horizontal axis Z are displaced diagonally via the pivot joints 9, 19, i.e., in the horizontal and vertical directions, depending on the pivot angle, i.e., up and to the left in the view shown. The displacement of the long leg 6' of the first branch takes place due to the length ratios of the respective legs 6', 6", 7', 7" both in the horizontal direction and in the vertical direction by a greater amount than the displacement of the long leg 7' of the second branch 7. The distal ends of the long legs 6', 7' are also moved and act on the trocar holder 10 via the connecting shafts 13a, 13b. Since the connection at the connecting shafts 13a, 13b with the trocar holder 10 is rotatable, the trocar holder 10 is not raised or shifted, but is rotated or pivoted about the stationary rotary point D of the trocar 5 lying on the horizontal axis Z, which is at the intersection of an imaginary central axis of the trocar 5 and the horizontal axis Z. Consequently, the trocar 5 is pivoted about the rotary point D relative to the starting position into a changed position (in this case, initially FIG. 6). The instrument tip is moved to the right in the perspective shown. Viewed from the proximal end of the holding device 1, i.e., when looking from the coupling portion K along the pivoting mechanism 12, this corresponds to a movement back, i.e., towards the proximal end. A movement towards the distal end, i.e., a forward movement, is brought about analogously, in the view of FIGS. 5 to 7, by a counterclockwise rotation on the terminal pivot joints 8, 18.

In FIG. 6, the holding device 1 is shown in a center position, i.e., in the zero position: The surgical instrument 2 is aligned completely vertically, i.e., neither tilted nor pivoted. However, this does not have to correspond to an actual zero position immediately when the trocar 5 is set; the trocar 5 can of course be set in a different alignment, as is medically expedient for the respective operation. The fastening of the trocar 5 to the holding device 1 can take place before or after the trocar 5 is set for the surgical operation; in the second case, the holding system 1 is initially set at least approximately to match the alignment of the trocar 5.

A further clockwise rotation on one of the terminal pivot joints 8, 18 causes the change from the new starting position of the trocar in FIG. 6 to the position of the holding device 1 shown in FIG. 7. The pivoting movement is prevented via the pivoting brake 16, which in the drawings acts on the terminal pivot joint 18 of the second branch 7, but in other embodiments can also be arranged on the terminal pivot joint 8 of the first branch 6 or on both. The pivoting brake 16 must correspondingly be released or set, depending on whether the surgical instrument 2 is to be held or pivoted by the holding device 1.

Figure 4:
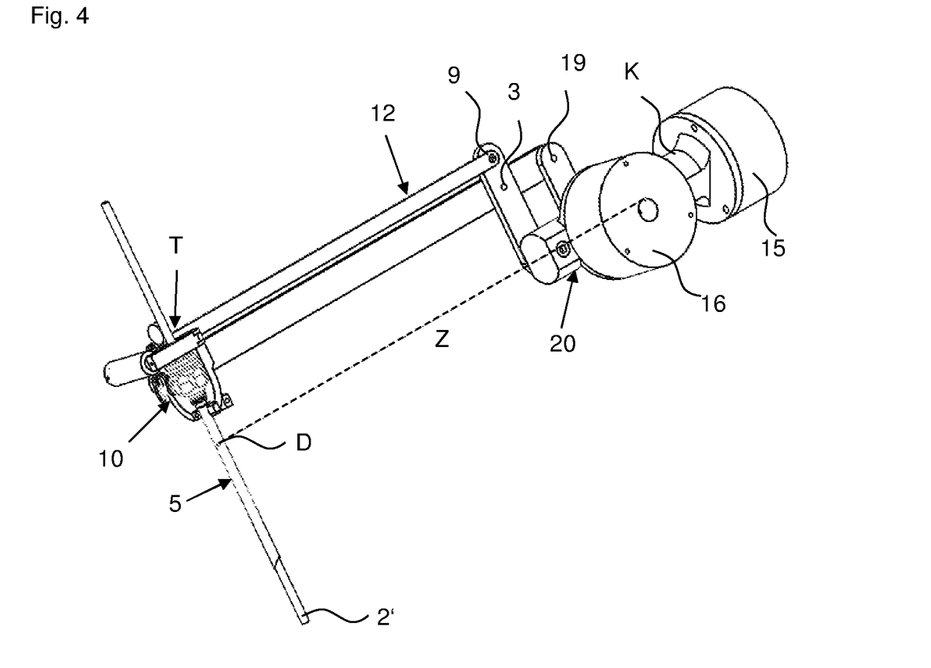
FIG. 4 is a perspective view of the passive holding device in the tilted position.

In FIG. 4, the holding device 1 is shown in a tilted position compared to FIG. 1, which position can be brought about by a further type of actuation of the pivoting mechanism 12. The position of the trocar shown in FIG. 1 is now referred to as the starting position. When the pivot joint arranged in the coupling portion K is actuated, it is deflected by a predetermined tilt angle, which is structurally unlimited in both directions (in this case, too, starting from a center position according to FIG. 6) so that the tilting could be carried out endlessly, but may be limited by the environmental conditions during the operation. As a result, the coupling portion K and the tilting brake 15 arranged therein are not moved. The pivoting mechanism 12, which is rotatably connected to the coupling portion K via the elongated holding portion 4, and the trocar holder 10 are rotated about the horizontal axis Z (dashed lines), resulting in a tilting of the held trocar 5 relative to the starting position about the rotary point D into the changed position in FIG. 4. As a result, the surgical instrument 2 guided in the trocar is also tilted. The instrument tip 2' is moved to the right in the drawing; viewed from the proximal end of the holding device 1, i.e., from the coupling portion K, this corresponds to a movement to the left. Tilting in the other direction is implemented in the same way. The maximum tilt angle is also limited by how inclined the trocar 5 can be arranged in the point of entry of the body at which point the rotary point D is located.

A tilting brake 15 is arranged on the coupling portion K with which the rotary joint located in the coupling portion K is braked, i.e., the tilting movement can be slowed down or completely prevented. The tilting brake 15, which, for example, like the other brakes 14, 16, can be a drum brake, is always effective in a preferred embodiment, provided that the braking effect is not suppressed in order to be able to execute a movement. To fix the current position of the surgical instrument 2, no additional manipulation has to be undertaken and no current has to be supplied. This also applies to the pivoting brake 16 and the instrument brake 14. The brakes 14, 15, 16 shown schematically do not have to have the shape shown and can be encased.

By superimposing the two possible changes in position of the trocar 5 (and thus of the surgical instrument 2) and the translational movement of the instrument 2 within the trocar 5, almost any coordinates in space for the instrument tip 2' can be set. The setting of the position of the holding device 1, i.e., moving around the joints and possibly releasing the brakes, is electronically controlled in preferred embodiments, whereby a precise, point-accurate solution is implemented.

As an example of the possibility of equipping the passive holding device 1 with sensors in order to determine the current position/orientation or the movement of the surgical instrument 2, a roller wheel 17 is arranged as a sensor 17 on the trocar holder 10 at the instrument brake 14 to measure the translational movement of the surgical instrument 2 and thus the penetration depth into the human body, for example into the abdominal cavity. Sensors can also be dispensed with entirely if, in a simple embodiment, the instrument position is not evaluated.

For this purpose, however, a plurality of sensors, which can be position, acceleration, or other sensors and which can form coordinated sensory measuring units, can be arranged on the holding device 1. Indirect detection via the pivot joint and the terminal pivot joint(s) 8, 18 is particularly useful, so that it is not the instrument movement itself that is detected (except possibly translation/rotation, e.g., via the roller wheel 17), but rather the change in position transmitted by the holding device 1 to the instrument 2 via pivoting by means of the pivoting mechanism 12 or tilting of the pivoting mechanism 12 by means of the rotary joint located in the coupling portion K. A common power supply can also be used in this way. An evaluation unit (not shown) can determine the current position of the surgical instrument 2, in particular the instrument tip 2', from the collected data.

The surgical instrument 2 is shown only schematically in the drawings; it can be an instrument 2 of any function, which at a distal end or portion around the instrument tip 2' has devices such as staplers, measuring devices, etc. or special shapes, e.g., has grippers, hooks, scissors, knives, clamps. Electrosurgical instruments and endoscopes are also included. In particular, a handle for manipulating the instrument 2 can be arranged at the proximal end. Alternatively, the instruments 2 can be electronically controlled or remotely controllable. Because almost any trocars 5 can be clamped into the trocar holder 10, in particular standard trocars 5, which have also been used frequently in microsurgery up to now, the choice of manageable instruments 2 is also diverse.

The holding device 1 should be accessible for hygienic treatments such as autoclaving. For this purpose, for reasons of hygiene, parts of the holding device 1 can also be received in a housing (not shown) that is easy to disinfect.

In order to form a modular surgical system, it is sufficient in the simple case to arrange a passive holding device 1 with a trocar 5 to be held therein and a (micro)surgical instrument 2, as shown in the drawings for illustration purposes. For more complex systems, a plurality of holding devices 1, possibly also active holding devices, are used.

Figure 8:
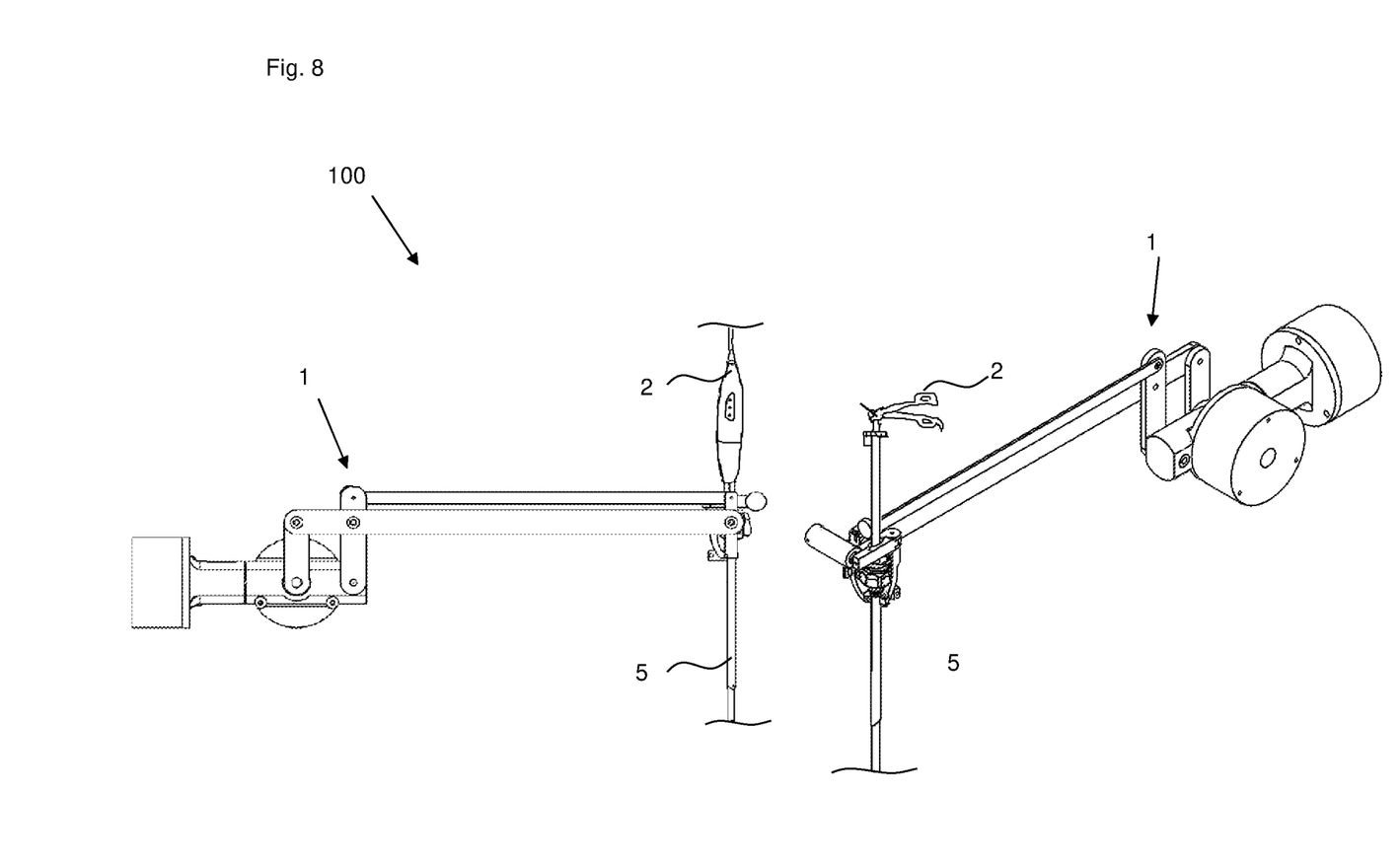
FIG. 8 shows a modular surgical system with two passive holding devices.

FIG. 8 shows a modular surgical system 100 with two passive holding devices 1, the surgical instruments 2 guided in the trocar 5 being an endoscope 2 and another surgical instrument 2 with a handle. Each holding device 1 has its own rotary point D (see, for example, FIG. 4), which lies in the abdominal wall at the respective point of entry into the abdominal cavity and around which the four degrees of freedom of movement of the surgical instrument 2 can be used. Alternatively, if the respective surgical instrument 2 is not to be moved, it can be held and fixed in its set position without the intervention of the surgical personnel.

Three or more holding devices with respective surgical instruments are also conceivable as a modular surgical system, with active holding devices also being able to be integrated in addition to the passive holding devices. Furthermore, modules for position determination, data evaluation, and/or control can be added in order to automatically execute the movement of an instrument that can be actuated in an active holding device and to couple it to the movement of an instrument that can be actuated in a passive holding device, the current position and orientation of which is detected by the position determination system.

It should be apparent that the foregoing relates only to the preferred embodiments of the present application and the resultant patent. Numerous changes and modification may be made herein by one of ordinary skill in the art without departing from the general spirit and scope of the invention as defined by the following claims and the equivalents thereof.

LIST OF REFERENCE SIGNS

| | |
|---|---|
| 1 | Passive holding device |
| 100 | Modular surgical system |
| 2 | Surgical instrument |
| 2' | Instrument tip (distal end) |
| 3 | Coupling point |
| 4 | Elongated holding portion |
| 5 | Trocar |
| 6 | First branch |
| 6' | Long leg first branch |
| 6" | Short leg first branch |
| 7 | Second branch |
| 7' | Long leg second branch |
| 7" | Short leg second branch |
| 8 | Terminal pivot joint first branch |
| 9 | Pivot joint first branch |
| 10 | Trocar holder |
| 11 | Gripping device |
| 11' | Receptacle |
| 12 | Pivoting mechanism |
| 13a | Connecting shaft first branch |
| 13b | Connecting shaft second branch |
| 14 | Instrument brake |
| 15 | Tilting brake |
| 16 | Pivoting brake |
| 17 | Roller wheel |
| 18 | Terminal pivot joint second branch |
| 19 | Pivot joint second branch |
| 20 | Fastening device |
| 21 | Clamp |
| 22 | Tripod |

| | |
|---|---|
| 23 | Tripod arm |
| 24 | Connector |
| D | Rotary point |
| K | Coupling portion |
| T | Distal end pivoting mechanism |
| Z | Horizontal axis |

We claim:

1. Passive holding device designed for handling a trocar which holds or guides a surgical instrument during a surgical operation, the passive holding device having a fastening device with a coupling portion, and wherein the trocar can be fastened to a connecting device via a trocar holder and can be fastened to the fastening device via said connecting device, characterized in that
 a pivoting mechanism is connected to the coupling portion via a rotary joint located in the coupling portion so as to be rotatable about a horizontal axis of the coupling portion, and forms the connecting device,
 wherein the pivoting mechanism has two L-shaped branches arranged parallel to one another, each of which has one short leg which is connected to a long leg via a pivot joint, wherein, on the coupling portion side, the ends of the short legs of each branch lying next to one another with an elongated holding portion of the fastening device are each connected via a terminal pivot joint, and wherein the short leg of the first branch is longer than the short leg of the second branch, is arranged at a distal end of the elongated holding portion and is connected to the long leg via a rotary shaft of the second branch, and wherein
 the trocar holder is pivotably attached to a distal end of the pivoting mechanism which has a gripping device which can be brought into engagement with the trocar and which has an instrument brake for operative coupling with the surgical instrument, and wherein
  a tilting brake is arranged at a proximal end of the coupling portion, which is operatively connected to the rotary joint located in the coupling portion, and
  a pivoting brake is arranged at the coupling portion which is operatively connected to at least one of the terminal pivot joints of the pivoting mechanism.

2. Holding device according to claim 1, characterized in that the trocar holder is coupled to the distal ends of the long legs of the branches of the pivoting mechanism via a respective connecting shaft, wherein the connecting shafts provide the pivotable attachment of the trocar holder to the pivoting mechanism, which is retractable.

3. Holding device according to claim 1, characterized in that at least one brake from the group comprising the instrument brake, the tilting brake, and the pivoting brake, is designed as a passive brake.

4. Holding device according to claim 1, characterized in that the holding device has a sensory measuring unit in order to determine a change in position or orientation of the surgical instrument, wherein
 there is a sensory measuring unit on the rotary joint, which is designed to detect a tilting movement of the holding device and/or
 a sensory measuring unit is present on at least one of the terminal pivot joints, which is designed to detect a pivoting movement of the holding device, and/or
 there is a sensory measuring unit on the trocar holder which is designed to detect a translational and/or rotational movement of the surgical instrument,
 wherein the sensory measuring unit has at least one sensor.

5. Holding device according to claim 4, characterized in that the sensor of the sensory measuring unit, which is present on the trocar holder, is a roller wheel.

6. Holding device according to claim 4, characterized in that, the sensor of the sensory measuring unit, which is present on the trocar holder, is a magnetic sensor or a capacitive sensor which is designed to interact with a magnetic measuring tape or a capacitive measuring tape for signal transmission which is present on the surgical instrument which is held or guided in the trocar.

7. Modular surgical system, which has at least one passive holding device and the trocar held by it and the surgical instrument which is held or guided in the trocar, characterized in that the passive holding device is the passive holding device according to claim 1.

8. Modular surgical system according to claim 7, characterized in that the system has a position determination system with an output unit and at least two holding devices, wherein at least one of the holding devices is an active holding device which has a control unit operatively coupled to the output unit and is designed to automatically move a further surgical instrument received in the active holding device.

9. Modular surgical system according to claim 8, characterized in that the position determination system is an optical or electromagnetic position determination system.

10. Method for operating the passive holding device according to claim 1 for handling the trocar which holds or guides the surgical instrument during a surgical operation and which is fastened to the passive holding device via the trocar holder, wherein while holding a stationary rotary point a change in position of the trocar is effected by actuating the pivoting mechanism.

* * * * *